(12) United States Patent
Sturla et al.

(10) Patent No.: US 6,495,119 B1
(45) Date of Patent: Dec. 17, 2002

(54) AEROSOL DEVICE CONTAINING A POLYCONDENSATE COMPRISING AT LEAST ONE POLYURETHANE AND/OR POLYUREA UNIT

(75) Inventors: Jean-Michel Sturla, Boulogne Billancourt (FR); Jean-Luc Bremenson, Paris (FR); François Le Bourhis, Aubervilliers (FR); Arnaud Vilbert, Villeneuve la Garenne (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/385,015

(22) Filed: Aug. 27, 1999

(30) Foreign Application Priority Data

Aug. 27, 1998 (FR) .............................. 98 10780

(51) Int. Cl.⁷ .............................. A61L 9/14; A61K 7/11; A61K 7/00; A61K 47/32; C08G 59/00
(52) U.S. Cl. ...................... 424/45; 424/70.11; 424/401; 424/70.12; 424/47; 514/772.1; 514/63; 514/770; 514/880
(58) Field of Search .............................. 424/70.11, 401, 424/45, 70.12, 47; 514/772.1, 63, 770, 880

(56) References Cited

U.S. PATENT DOCUMENTS

| 4,931,062 A | | 6/1990 | Bay et al. | |
| 5,626,840 A | * | 5/1997 | Thomaides et al. | 424/70.11 |
| 5,643,581 A | | 7/1997 | Mougin et al. | |
| 5,653,963 A | * | 8/1997 | Beitone et al. | 424/47 |
| 6,166,093 A | * | 12/2000 | Mougin et al. | 514/772.1 |

FOREIGN PATENT DOCUMENTS

| DE | 42 25 045 | 2/1994 |
| DE | 42 41 118 | 6/1994 |
| DE | 43 38 849 | 5/1996 |
| DE | 195 41 326 | 5/1997 |
| EP | 0 542 072 | 5/1993 |
| EP | 0 582 152 | 2/1994 |
| EP | 0 619 111 | 10/1994 |
| EP | 0 636 361 | 2/1995 |
| EP | 0 637 600 | 2/1995 |
| EP | 0 648 485 | 4/1995 |
| EP | 0 745 373 | 12/1996 |
| EP | 0 751 162 | 1/1997 |
| EP | 0 756 860 | 2/1997 |
| EP | 0 779 310 | 6/1997 |
| EP | 0 838 211 | 4/1998 |
| EP | 0 838 212 | 4/1998 |
| FR | 2 743 297 | 7/1997 |
| FR | 2 749 568 | 12/1997 |
| WO | WO 93/23009 | 11/1993 |
| WO | WO 94/03510 | 2/1994 |
| WO | WO 96/14049 | 5/1996 |
| WO | WO 96/14050 | 5/1996 |
| WO | WO 97/15275 | 5/1997 |
| WO | WO 97/25021 | 7/1997 |
| WO | WO 98/20833 | 5/1998 |

OTHER PUBLICATIONS

English language Derwent Abstract of DE 42 25 045.
English language abstract of EP 0 542 072.
English language abstract of EP 0 779 310.
Derwent Publications, Ltd., London, GB; AN 93–410762 (JP 05 310535).
English language Derwent Abstract of DE 42 41 118.
English language Derwent Abstract of DE 44 38 489.
English language Derwent Abstract of DE 195 41 326.
English language Derwent Abstract of EP 0 636 631.
English language Derwent Abstract of EP 0 637 600.
English language Derwent Abstract of EP 0 648 485.
English language Derwent Abstract of EP 0 745 373.
English language Derwent Abstract of EP 0 751 162.
English language Derwent Abstract of EP 0 756 860.
English language Derwent Abstract of FR 2 743 297.
English language Derwent Abstract of FR 2 749 568.

* cited by examiner

Primary Examiner—Frederick Krass
Assistant Examiner—Clinton Ostrup
(74) Attorney, Agent, or Firm—Finnegan, Henderson, Farabow, Garrett & Dunner, L.L.P.

(57) ABSTRACT

The invention relates to aerosol devices comprising a container which contains, in a cosmetically acceptable medium, a multiblock polymer comprising at least one polyurethane and/or polyurea unit, these devices being suitable for obtaining an initial flow rate of aerosol composition of less than or equal to 0.75 gram per second. The invention is also directed towards a process for shaping or maintaining the hairstyle, comprising the use of these devices, as well as their use for the manufacture of a lacquer or an aerosol spray.

32 Claims, No Drawings

AEROSOL DEVICE CONTAINING A POLYCONDENSATE COMPRISING AT LEAST ONE POLYURETHANE AND/OR POLYUREA UNIT

The invention relates to aerosol devices comprising a container which contains, in a cosmetically acceptable medium, a polycondensate, such as a multiblock polymer, comprising at least one polyurethane and/or polyurea unit. The devices can further comprise at least one polyol, an organic solvent, and a propellant gas. The devices are suitable for obtaining an initial flow rate of aerosol composition of less than or equal to 0.75 gram per second. The invention is also directed toward a process for shaping or maintaining a hairstyle, comprising the use of these devices, as well as their use for the manufacture of lacquers or aerosol sprays.

Fixing of the hairstyle is an important element of styling which can comprise maintaining the shape already given or in shaping the hair and fixing it simultaneously.

Hair products for shaping and/or maintaining the hairstyle which are the most common on the cosmetics market are spray compositions comprising a solution, usually an alcoholic or aqueous solution, and one or more materials, generally polymer resins (also known as fixing materials), the function of which is to form welds between the hairs. The solution also often includes various cosmetic adjuvants. The solution can be packaged, for example, in a suitable aerosol container placed under pressure using a propellant. The construction and operation of such aerosol containers is well known to those skilled in the art.

The packaging in aerosol form is especially practical for the user, who obtains fairly homogeneous distribution of the product without difficulty. However, this type of packaging has the drawback of giving rise to a release of volatile organic compounds (VOCs) that are harmful to the environment. They originate in particular from the amount of organic solvent used and of propellant gas chosen to manufacture the composition. Manufacturers thus are in search of cosmetic compositions which can be packaged in aerosol form and which expel very low amounts of volatile organic compounds.

The quality of the spraying obtained by means of an aerosol device, i.e., essentially the distribution of the droplets in space at the nozzle outlet, can depend on the chemical constitution of the composition used. A great amount of attention is thus given to the preparation of aerosol devices which give rise to an optimum spraying quality.

Patent DE 195 41 326 discloses the preparation of styling compositions comprising a polymer containing polyurethane units as fixing polymer. However, the devices can be improved in particular as regards the cosmetic properties which they give to the hair, while at the same time offering better spraying quality.

The inventors have discovered that it is possible to prepare aerosol devices which satisfy the requirements expressed above by choosing the proper combination of a composition (e.g., a hair styling composition) and a means for distributing this composition.

The subject of the invention is thus an aerosol device comprising 1) a container containing a composition, such as a hair styling composition, where the composition is formed of a fluid and at least one propellant, and 2) a means for distributing the composition. The aerosol device is characterized in that:

(1) the composition comprises, in a cosmetically acceptable medium, at least one polycondensate comprising at least one sequence chosen from polyurethanes and polyureas; and (2) the device is suitable for giving an initial flow rate of aerosol composition of less than or equal to 0.75 gram per second.

Another subject of the invention relates to a process for shaping or maintaining a hairstyle, comprising the use of this aerosol device.

Yet another subject of the invention relates to the use of this device for the manufacture of a lacquer or an aerosol spray.

Examples of polycondensates comprising at least one polyurethane and/or polyurea compound according to the present invention include those described in patents EP 0,751,162, EP 0,637,600, FR 2,743,297, and EP 0,648,485, all assigned to the present assignee, as well as patents EP 0,656,021 and WO 94/03510 from the company BASF, and EP 0,619,111 from the company National Starch. The disclosures of all of these documents are specifically incorporated herein by reference.

The polycondensates used in accordance with the invention can be soluble in the cosmetically acceptable medium, in particular after neutralization with an organic or inorganic base, or alternatively can form a dispersion in this medium. In the latter case, the dispersion can generally comprise at least 0.05% of surfactant, which allows the polycondensate to form a dispersion and to be maintained in dispersion.

According to the invention, any type of surfactant can be used in the dispersion, including a nonionic surfactant. In embodiments, the average size of the polycondensate particles in the dispersion is between 0.1 and 1 micron (micrometer), inclusive.

By way of example, the polycondensate can be formed by an arrangement of blocks, this arrangement being obtained in particular from:

(1) at least one compound which contains at least two active hydrogen atoms per molecule;

(2) at least one diol containing at least one functional group chosen from acid radicals and salts thereof; and (3) at least one isocyanate chosen from di- and polyisocyanates. Compound (1) can be chosen from the group comprising diols, diamines, polyesterols, polyetherols, and mixtures thereof.

In certain embodiments, compound (1) can be a linear polyethylene or polypropylene glycol, in particular those which are obtained by a reaction of ethylene oxide or propylene oxide with water or diethylene or dipropylene glycol in the presence of sodium hydroxide as catalyst. These polyglycols generally have a molecular weight of between about 600 and 20,000.

In embodiments, the organic compounds are those which have mercapto, amino, carboxyl, or hydroxyl groups. Among these, mention may be made more particularly of polyhydroxy compounds such as polyether diols, polyester diols, polyacetal diols, polyamide diols, polyesterpolyamide diols, poly(alkylene ether) diols, polythioether diols, and polycarbonate diols.

The polyether diols can be, for example, the condensation products of ethylene oxide, of propylene oxide, or of tetrahydrofuran, their copolymerization or condensation products, which may be grafted or blocks, such as mixtures of condensates of ethylene oxide and propylene oxide, and the products of polymerization of olefins, at high pressure, with alkylene oxide condensates. Suitable polyethers can be prepared, for example, by condensation of alkylene oxides and polyhydric alcohols, such as ethylene glycol, 1,2-propylene glycol, and 1,4-butanediol.

The polyester diols, polyesteramides, and polyamide diols are, in embodiments, saturated and can be obtained, for example, from the reaction of saturated or unsaturated polycarboxylic acids with polyhydric alcohols, diamines, or polyamines. Adipic acid, succinic acid, phthalic acid, terephthalic acid, and maleic acid can be used, for example, to prepare these compounds. Polyhydric alcohols that are suitable for preparing the polyesters include, for example, ethylene glycol, 1,2-propylene glycol, 1,4-butanediol, neopentyl glycol, and hexanediol. Amino alcohols, for example ethanolamine, can also be used. Diamines that are suitable for preparing the polyesteramides include, but are not limited to, ethylenediamine and hexamethylenediamine.

Suitable polyacetals can be prepared, for example, from 1,4-butanediol or from hexanediol and from formaldehyde. Suitable polythioethers can be prepared, for example, by condensation reaction between thioglycols, either alone or in combination with other glycols such as ethylene glycol, 1,2-propylene glycol or with other polyhydroxylated compounds. Polyhydroxylated compounds already containing urea or urethane groups, and natural polyols, which can be further modified, for example castor oil and carbohydrates, can also be used.

In certain embodiments, compound (1) is a polyesterol, in particular a polyester diol formed by the reaction of at least one (di)polyol ($1_a$) and at least one acid ($1_b$). The (di)polyol ($1_a$) can be chosen from the group comprising neopentyl glycol, 1,4-butanediol, hexanediol, ethylene glycol, diethylene glycol, propylene glycol, butylene glycol, neopentyl glycol, and (di)polyethylene glycol. The acid ($1_b$) can be chosen from the group comprising phthalic acid, isophthalic acid, adipic acid, and (poly)lactic acid.

A hydroxycarboxylic acid such as dimethylol-propanoic acid (DMPA), or a 2,2-hydroxymethylcarboxylic acid can be used as compound (2). In general, compound (2) is useful as a coupling block. In certain embodiments, compound (2) comprises at least one poly((α-hydroxydiolcarboxylic) acid). In certain other embodiments, compound (2) is chosen from the group comprising 2,2-di(hydroxy-methyl)acetic acid, 2,2-dihydroxymethylpropionic acid, 2,2-dihydroxymethylbutyric acid, and 2,2-dihydroxymethylpentanoic acid.

The isocyanate compound (3) can be chosen from the group comprising hexamethylene diisocyanate, isophorone diisocyanate (IPDI), toluylene diisocyanate, diphenylmethane 4,4'-diisocyanate (DPMD), dicyclohexylmethane 4,4'-diisocyanate (DCMD), methylenebis(p-phenyl) diisocyanate, methylenebis(4-cyclohexyl isocyanate), isophorone diisocyanate, toluene diisocyanate, 1,5-naphthalene diisocyanate, 4,4'-diphenylmethane diisocyanate, 2,2'-dimethyl-4,4'-diphenylmethane diisocyanate, 1,3-phenylene diisocyanate, 1,4-phenylene diisocyanate, mixtures of 2,4- and 2,6-toluene diisocyanate, 2,2'-dichloro-4,4'-diisocyanatodiphenylmethane, 2,4-dibromo-1,5-diisocyanatonaphthalene, butane 1,4-diisocyanate, 1,6-hexane diisocyanate, and 1,4-cyclohexane diisocyanate.

The polycondensate can be formed using at least one additional compound (4), which generally serves to extend the polycondensate chain. These compounds (4) can be chosen from the group comprising saturated or unsaturated glycols such as ethylene glycol, diethylene glycol, neopentyl glycol or triethylene glycol; amino alcohols such as ethanolamine, propanolamine, or butanolamine; heterocyclic, aromatic, cycloaliphatic, and aliphatic primary amines; diamines; carboxylic acids such as aliphatic, aromatic or heterocyclic carboxylic acids, for instance oxalic acid, succinic acid, glutaric acid, adipic acid, sebacic acid or terephthalic acid; and amino carboxylic acids. In certain embodiments, compound (4) is an aliphatic diol.

The polycondensates in accordance with the invention can also be formed from at least one additional compound (5) having a silicone skeleton. In certain embodiments, compound (5) is a polysiloxane, polyalkylsiloxane, polyarylsiloxane, or a mixture thereof. In certain embodiments, polyethylsiloxanes, polymethylsiloxanes, and polyphenylsiloxanes, optionally containing hydrocarbon-based chains grafted onto the silicon atoms, can be used.

In certain embodiments, the polyurethane and/or polyurea compounds of the polymer can have a repeating base unit corresponding to the general formula (I):

—X—B—X—CO—NH—R—NH—CO— (I)

in which:

X represents O and/or NH,

B is a divalent hydrocarbon-based radical, this radical being substituted or unsubstituted, and R is a divalent substituted or unsubstituted radical chosen from aromatic alkylene radicals, $C_1$ to $C_{20}$ aliphatic radicals, and $C_1$ to $C_{20}$ cycloaliphatic radicals.

In certain embodiments, radical B is a $C_1$ to $C_{30}$ radical and bears a group containing one or more carboxylic functional groups and/or one or more sulphonic functional groups. In these embodiments, the carboxylic and/or sulphonic functional groups can be in free form or else partially or totally neutralized with an inorganic or organic base.

The radical R can be chosen from the radicals corresponding to the following formulae:

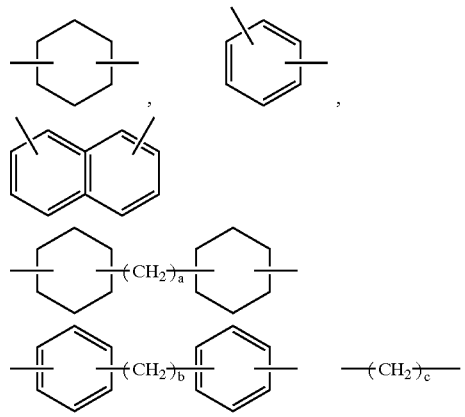

in which b is an integer between 0 and 3, inclusive, and c is an integer between 1 and 20, inclusive, such as between 2 and 12, inclusive.

In certain embodiments, radical R is chosen from hexamethylene, 4,4'-biphenylenemethane, 2,4- and/or 2,6-tolylene, 1,5-naphthylene, p-phenylene and methylene-4,4-bis-cyclohexyl radicals, and the divalent radicals derived from isophorone.

The polycondensate used in accordance with the invention (comprising at least one polyurethane and/or polyurea compound) can also comprise at least one polysiloxane in which the repeating base unit corresponds, for example, to the formula (II):

—X—P—X—CO—NH—R—NH—CO— (II)

in which:

P is a polysiloxane segment,

X is chosen from O and NH, and

R is chosen from divalent substituted and unsubstituted radicals chosen from aromatic alkylene radicals, $C_1$ to $C_{20}$ aliphatic radicals, and $C_1$ to $C_{20}$ cycloaliphatic radicals.

In certain embodiments, the polysiloxane segment P corresponds to the formula (III):

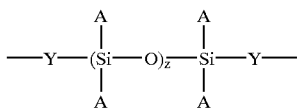

(III)

in which:
the radicals A, which can be identical or different, are chosen from, on the one hand, $C_1$ to $C_{20}$ monovalent hydrocarbon-based radicals which are free or substantially free of ethylenic unsaturation and, on the other hand, aromatic radicals, Y is chosen from divalent hydrocarbon-based radicals, and Z is chosen from integers such that the average molecular weight of the polysiloxane segment is between 300 and 10,000, inclusive.

In general, the divalent radical Y is chosen from alkylene radicals of formula —$(CH_2)_a$—, in which a represents an integer which can be between 1 and 10, inclusive.

The radicals A can be, but is not necessarily, chosen from alkyl radicals, such as methyl, ethyl, propyl, isopropyl, butyl, pentyl, hexyl, octyl, decyl, dodecyl, and octadecyl radicals; cycloalkyl radicals, in particular the cyclohexyl radical; aryl radicals, including phenyl and naphthyl; arylalkyl radicals, in particular benzyl and phenylethyl; and tolyl and xylyl radicals.

In certain embodiments, the fluid comprises an organic solvent and the weight ratio of the propellant gas to the organic solvent is greater than or equal to 1.75:1.

The distribution means, which forms a part of the aerosol device, can comprise a distribution valve controlled by a distribution head, which itself can comprise a nozzle through which the aerosol composition is vaporized. All of these components are well known to those skilled in the art and thus no drawing is needed because a drawing is not necessary to understand the subject matter of the invention.

In accordance with the invention, the initial flow rate of aerosol composition is measured for a temperature in the region of 20° C. inside the aerosol device. In practice, the aerosol device is placed at room temperature and the flow rate of aerosol composition is measured when the thermodynamic equilibrium is reached.

The initial flow rate is the average amount of product leaving the previously unused aerosol device, over fifty seconds. It is expressed in grams per second.

The initial flow rate of the aerosol composition ($F_{AC}$) corresponds to the amount of aerosol composition (fluid+ propellant) per unit of time leaving the previously unused aerosol device. It is expressed in mg/s and is measured by the difference between the weight of the aerosol before ($M_0$) and after ($M_1$) 10 seconds of vaporization:

$$F_{AC}=(M_0-M_1)/10.$$

The aerosol device according to the invention is suitable for obtaining an initial flow rate of aerosol composition of generally less than or equal to 0.7 gram per second.

The initial flow rate of aerosol composition from the devices according to the invention depends, on the one hand, on the composition, and, on the other hand, on the distribution means, the two needing to be suitable in order to obtain the desired characteristics. The particular characteristics defined above can be obtained by selecting the appropriate distribution means and/or by modifying the formulation.

The valves which are suitable for the particular compositions above can generally be valves with a 0.33 mm internal restriction orifice, without an additional gas intake orifice and with a nozzle orifice measuring generally between 0.33 and 0.51 mm, inclusive. A press-button having a turbulent nozzle with a nozzle orifice between 0.4 and 0.5 mm, inclusive, in size can be used.

The polycondensates used in accordance with the invention can be soluble in the cosmetically acceptable medium or alternatively can form a dispersion in this medium. In the latter case, the dispersion can generally comprise at least 0.05% surfactant, which allows the polycondensate to form a dispersion and to be maintained in dispersion.

According to the invention, any type of surfactant can be used in the dispersion, including a nonionic surfactant. The average size of the polycondensate particles in the dispersion is, in certain embodiments, between 0.1 and 1 micron (micrometer), inclusive.

The composition in accordance with the invention generally comprises, in relative proportions by weight relative to the total weight of the composition, between 0.1 and 20%, inclusive, of the polycondensate comprising at least one sequence chosen from polyurethanes and polyureas. In certain embodiments, it comprises between 1 and 15%, inclusive, by weight, of polycondensate. In certain embodiments, it comprises between 2 and 8%, inclusive, by weight, of polycondensate.

The composition can comprise between 7.5 and 70%, inclusive, by weight, of an organic solvent. In certain embodiments, it comprises between 10 and 50%, inclusive, by weight. In certain other embodiments, it comprises between 10 and 25%, inclusive, by weight, of the polycondensate.

In certain embodiments of the invention, the organic solvent is chosen from the group comprising $C_1$ to $C_4$ alcohols, such as ethanol and isopropanol; acetone; methyl ethyl ketone; methyl acetate; butyl acetate; ethyl acetate; dimethoxyethane; diethoxyethane; and mixtures thereof. In certain embodiments, ethanol is used.

The relative proportion by weight, relative to the total weight of the composition, of propellant gas in the composition can be between 15 and 85%, inclusive. In certain embodiments, the composition comprises between 25 and 60%, inclusive, by weight, of propellant. In certain other embodiments, the composition comprises between 30 and 50%, inclusive, by weight, of propellant.

In accordance with certain embodiments of the invention, gas which is soluble or insoluble in the composition, such as dimethyl ether, fluoro or non-fluoro hydrocarbons, the usual liquefied gases used in body-treating compositions, or a mixture of these propellant gases, can be used as propellant gas. In certain embodiments, dimethyl ether is used.

The compositions in accordance with the invention can moreover contain at least one cosmetic additive. Examples of these additives include, but are not limited to, fatty substances, thickeners, softeners, antifoaming agents, moisturizers, antiperspirants, basifying agents, dyes, pigments, fragrances, preserving agents, surfactants, hydrocarbon-based polymers, volatile and non-volatile silicones, such as anionic silicones, polyols, proteins, and vitamins.

In embodiments, at least one fixing polymer can be included in the composition. In certain embodiments, the fixing polymer is selected from nonionic, anionic, cationic, and amphoteric fixing polymers.

The invention may be understood more clearly with the aid of the non-limiting example below.

EXAMPLE

A device in accordance with the invention was prepared, containing the following composition.

| | |
|---|---|
| Lactic acid/ethylene glycol P (MIS-EG) dimethylolpropanoic acid (DMPA)-isophorone diisocyanate polyester polycondensate | 4% |
| Aminomethylpropanol | qs neutralization |
| Ethanol | 15% |
| Dimethyl ether | 35% |
| Demineralized water | qs 100% |

A valve was used comprising
a 0.33 mm nozzle orifice,
no additional gas intake orifice,
a 0.33 mm internal restriction orifice.
A press-button with a 0.45 mm outlet orifice turbulent nozzle was used. The initial flow rate measured at 20° C. is 0.65 gram per second.

What is claimed is:

1. An aerosol device comprising:
   (a) a container containing a composition formed of a fluid and at least one propellant, and
   (b) means for distributing the composition, wherein
      (i) the composition comprises, in a cosmetically acceptable medium, at least one polycondensate comprising at least one sequence chosen from polyurethanes and polyureas; and
      (ii) the device is suitable for giving an intitial flow rate of aerosol composition of less than or equal to 0.75 gram per second,
   wherein said at least one polycondensate is formed by an arrangement of blocks, this arrangement being obtained from:
      (1) at least one compound which contains at least two active hydrogen atoms per molecule;
      (2) at least one diol containing at least one functional group chosen from acid radicals and salts thereof; and
      (3) at least one isocyanate chosen from di- and polyisocyanates, wherein the (1) at least one compound is different than the (2) at least one diol.

2. The device according to claim 1, characterized in that the initial flow rate of aerosol composition is less than or equal to 0.7 gram per second.

3. The device according to claim 1, wherein the fluid contains an organic solvent, the weight ratio of the propellant to the organic solvent being greater than or equal to 1.75:1.

4. The device according to claim 3, comprising between 7.5 and 70%, inclusive, of said organic solvent, by weight of the total weight of the composition.

5. The device according to claim 3, comprising between 10 and 50%, inclusive, of said organic solvent, by weight of the total weight of the composition.

6. The device according to claim 3, comprising between 10 and 25%, inclusive, of said organic solvent, by weight of the total weight of the composition.

7. The device according to claim 1, wherein said at least one compound (1) is chosen from diols, diamines, polyesterols, and polyetherols.

8. The device according to claim 1, wherein said at least one diol (2) is a 2,2-hydroxymethylcarboxylic acid.

9. The device according to claim 1, wherein said at least one isocyanate (3) is chosen from hexamethylene diisocyanate, isophorone diisocyanate, toluylene diisocyanate, diphenylmethane 4,4'-diisocyanate dicyclohexylmethane 4,4'-diisocyanate, methylenebis(p-phenyl) diisocyanate, methylenebis(4-cyclohexyl isocyanate), isophorone diisocyanate, toluene diisocyanate, 1,5-naphthalene diisocyanate, 4,4'-diphenylmethane diisocyanate, 2,2'-dimethyl-4,4'-diphenylmethane diisocyanate, 1,3-phenylene diisocyanate, 1,4-phenylene diisocyanate, mixtures of 2,4- and 2,6-toluene diisocyanate, 2,2'-dichloro-4,4'-diisocyanatodiphenylmethane, 2,4-dibromo-1,5-diisocyanatonaphthalene, butane 1,4-diisocyanate, 1,6-hexane diisocyanate, and 1,4-cyclohexane diisocyanate.

10. The device according to claim 1, wherein the polycondensate is formed from at least one additional compound having a silicone skeleton.

11. The device according to claim 10, wherein the at least one additional compound having a silicone skeleton is chosen from polysiloxanes, polyalkylsiloxanes, and polyarylsiloxanes, and wherein said polysiloxanes, polyalkylsiloxanes, and polyarylsiloxanes optionally containing hydrocarbon-based chains grafted onto the silicon atoms.

12. The device according to claim 11, wherein the polyalkylsiloxane is chosen from polyethylsiloxanes and polymethylsiloxanes, and the polyarylsiloxane is chosen from polyphenylsiloxanes.

13. The device according to claim 1, wherein said at least one sequence chosen from polyurethanes and polyureas has a repeating base unit corresponding to the formula (I):

—X—B—X—CO—NH—R—NH—CO—      (I)

in which:
X is chosen from O and NH,
B is a hydrocarbon-based radical, this radical being substituted or unsubstituted, and
R is a divalent radical chosen from aromatic alkylene radicals, $C_1$ to $C_{20}$ aliphatic radicals, and $C_1$ to $C_{20}$ cycloaliphatic radicals, these radicals being substituted or unsubstituted.

14. The device according to claim 13, wherein B is a $C_1$ to $C_{30}$ divalent hydrocarbon-based radical.

15. The device according to claim 13, wherein radical R is chosen from hexamethylene, 4,4'-biphenylenemethane, 2,4- and/or 2,6-tolylene, 1,5-naphthylene, p-phenylene and methylene-4,4-bis-cyclohexyl radicals, and divalent radicals derived from isophorone.

16. The device according to claim 1, wherein the polycondensate has a repeating base unit corresponding to the formula (II):

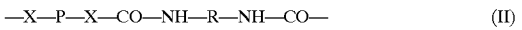

—X—P—X—CO—NH—R—NH—CO—      (II)

in which:
P is a polysiloxane segment,
X is chosen from O and NH, and
R is chosen from divalent substituted and unsubstituted radicals chosen from aromatic alkylene radicals, $C_1$ to $C_{20}$ aliphatic radicals, and $C_1$ to $C_{20}$ cycloaliphatic radicals.

17. The device according to claim 1, comprising between 0.1 and 20%, inclusive, of said polycondensate, by weight of the total weight of the composition.

18. The device according to claim 1, comprising between 1 and 15%, inclusive, of said polycondensate, by weight of the total weight of the composition.

19. The device according to claim 1, comprising between 2 and 8%, inclusive, of said polycondensate, by weight of the total weight of the composition.

20. The device according to claim 1, comprising between 15 and 70%, inclusive, of said propellant, by weight of the total weight of the composition.

21. The device according to claim 1, comprising between 25 and 60%, inclusive, of said organic solvent, by weight of the total weight of the composition.

22. The device according to claim 1, comprising between 30 and 50%, inclusive, of said organic solvent, by weight of the total weight of the composition.

23. The device according to claim 1, comprising a valve with a 0.33 mm internal restriction orifice, without an additional gas intake orifice and with a nozzle orifice measuring between 0.33 and 0.51 mm, inclusive.

24. The device according to claim 1, comprising a press-button having a turbulent nozzle, the nozzle orifice being between 0.4 and 0.5 mm, inclusive, in size.

25. The device according to claim 1, wherein the composition further comprises at least one cosmetic additive.

26. The device according to claim 25, wherein said at least one cosmetic additive is chosen from fatty substances, thickeners, softeners, antifoaming agents, moisturizers, antiperspirants, basifying agents, dyes, pigments, fragrances, preserving agents, surfactants, hydrocarbon-based polymers, silicones, volatile and non-volatile silicones, polyols, proteins, and vitamins.

27. The device according to claim 1, further comprising at least one fixing polymer chosen from nonionic, cationic, anionic, and amphoteric fixing polymers.

28. A device comprising:
 a) a composition,
  wherein said composition comprises
   Lactic acid/ethylene glycol P (MIS-EG) dimethylolpropanoic acid (DMPA)-isophorone diisocyanate polyester polycondensate,
   Aminomethylpropanol,
   Ethanol,
   Dimethyl ether, and
   Demineralized water; and
 b) a valve,
  wherein said valve comprises
   a 0.33 mm nozzle orifice, but no additional gas intake orifice,
   a 0.33 mm internal restriction orifice, and
   a press-button with a 0.45 mm outlet orifice turbulent nozzle.

29. The device according to claim 28, wherein the composition comprises:
 4%, by weight, lactic acid/ethylene glycol P (MIS-EG) dimethylolpropanoic acid (DMPA)-isophorone diisocyanate polyester polycondensate,
 a sufficient amount of aminomethylpropanol to neutralize the solution,
 15% by weight, ethanol,
 35%, by weight, dimethyl ether, and
 a sufficient amount of demineralized water to achieve 100% total weight.

30. The device according to claim 28, wherein the initial flow rate measured at 20° C. is 0.65 gram per second.

31. A process for shaping or maintaining a hairstyle, wherein said process comprises applying to hair a hair styling composition with an aerosol device comprising:
 (a) a container containing a composition formed of a fluid and at least one propellant, and
 (b) means for distributing the composition,
 said device characterized in that:
  (i) the composition comprises, in a cosmetically acceptable medium, at least one polycondensate comprising at least one sequence chosen from polyurethanes and polyureas; and
  (ii) the device is suitable for giving an initial flow rate of aerosol composition of less than or equal to 0.75 gram per second.

32. A process for the production of a hair spray, said process comprising expelling a composition contained in an aerosol device, wherein said device comprises:
 (a) a container containing said composition, and
 (b) means for distributing said composition,
 said device characterized in that:
  (i) said composition comprises, in a cosmetically acceptable medium,
   a fluid comprising at least one polycondensate, said polycondensate comprising at least one sequence chosen from polyurethanes and polyureas, and
   at least one propellant; and
  (ii) the device is suitable for giving an initial flow rate of aerosol composition of less than or equal to 0.75 gram per second.

* * * * *